United States Patent [19]

Jönsson et al.

[11] 3,947,451
[45] Mar. 30, 1976

[54] DERIVATIVES OF SUBSTITUTED ISOQUINOLINE 1,3-DIONES

[75] Inventors: Nils Åke Jönsson, Sodertalje; Lembit Mikiver, Jarna; Pinchas Moses, Solna, all of Sweden

[73] Assignee: AB Kabi, Stockholm, Sweden

[22] Filed: Sept. 11, 1972

[21] Appl. No.: 288,027

[30] Foreign Application Priority Data

Sept. 16, 1971 Sweden.............................. 11742/71

[52] U.S. Cl. 260/281 R; 260/247.5 FP; 260/268 BQ; 260/283 S; 260/268 BC; 260/286 R; 260/286 Q; 260/287 K; 260/289 K; 260/293.55; 260/326.1; 260/326 A; 260/471 A; 260/561 A; 260/281 SP; 424/250; 424/258; 424/274
[51] Int. Cl.² ........................................ C07D 217/24
[58] Field of Search......... 260/287 R, 256.4 Q, 281, 260/268 BC

[56] References Cited
UNITED STATES PATENTS

| | | | |
|---|---|---|---|
| 2,642,431 | 6/1953 | Ullyot............................. | 260/287 R |
| 3,274,194 | 9/1966 | Hayao............................. | 260/268 BC |
| 3,406,175 | 10/1968 | Lesher............................. | 260/281 |
| 3,457,272 | 7/1969 | Crook et al....................... | 260/287 R |
| 3,718,648 | 2/1973 | Beyerle et al.................... | 260/256.4 Q |

OTHER PUBLICATIONS

Burger, "Medicinal Chemistry," 1963, pp. 42, 497, Interscience Publishers.

"Chemical Abstracts", Meyer et al., from Arch. Pharm., (1970), Vol. 73, abs 45304a.

*Primary Examiner*—Donald G. Daus
*Assistant Examiner*—David E. Wheeler
*Attorney, Agent, or Firm*—Brumbaugh, Graves, Donohue & Raymond

[57] ABSTRACT

New pharmacodynamically active nitrogen containing heterocyclic compounds of the general formula

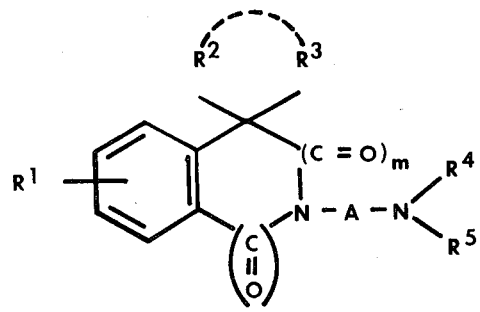

as well as methods of preparing the same; and pharmacodynamical compositions containing the same, preferably for treating psychiatric and psychosomatic diseases.

22 Claims, No Drawings

DERIVATIVES OF SUBSTITUTED ISOQUINOLINE 1,3-DIONES

The present invention relates to new pharmacodynamically active nitrogen containing heterocyclic compounds of the general formula

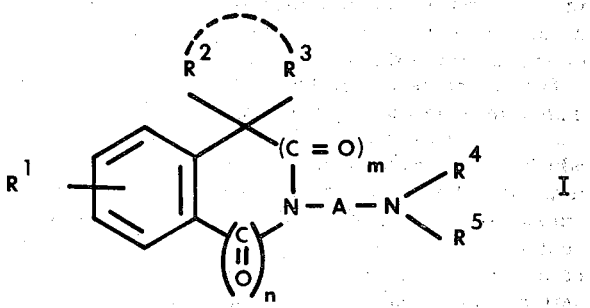

as well as to methods of preparing the same; in formula I m and n are 0 or 1 and chosen in such a way that $m + n \geq 1$, A is an ethylene or trimethylene radical, which may be substituted by a methyl group, or A signifies a possibly α-alkylated acetyl group, which is in an amidelike manner connected to

and contains up to 4 carbon atoms in the alkyl radical, $R^1$ is hydrogen, halogen or a nitro group $R^2$ and $R^3$ are saturated or unsaturated aliphatic hydrocarbon residues of up to 6 carbon atoms, which taken together with the carbon atom to which they are bonded may form a ring, which may be substituted by an oxo or a hydroxy group, $R^4$ and $R^5$ are hydrogen or alkyl radicals of at most 6 carbon atoms or $R^4$ and $R^5$ together with the nitrogen form a pyrrolidine, a piperidine, a morpholine, a piperazine, an $N^4$-lower alkylpiperazine or an $N^4$-β-hydroxyethylpiperazine ring, In case A does not signify a possibly alkylated acetyl radical, the invention also comprises the corresponding amine oxides and quarternary ammonium compounds as well as salts of the basic compounds with physiologically acceptable acids.

In those cases where the compounds of formula I may occur as pairs of optical antipodes, the invention comprises the racemic mixture as well as each of the antipodes separately.

The new compounds can be prepared by reactions known per se, and the combination of the steps of synthesis in the particular synthetical route is dependent on the groups $R^1$–$R^5$ as well as on m and n.

In a preferred embodiment, a compound of formula

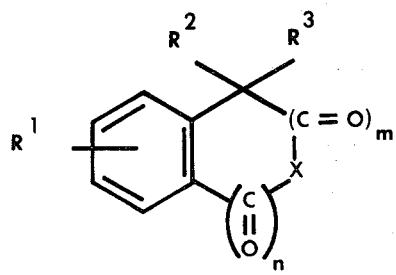

in which $R^1$, $R^2$ and $R^3$, m and n are as defined above and X signifies NH, preferably in the form of a salt with a suitable cation, for instance alkali metal ions or quarternary ammonium ions, is reacted with a compound of formula $$Y - Z \qquad \qquad III$$

in which Y signifies a reactive group, which together with the hydrogen or the cation at the imide respectively the lactame nitrogen can be split off while forming a compound of formula

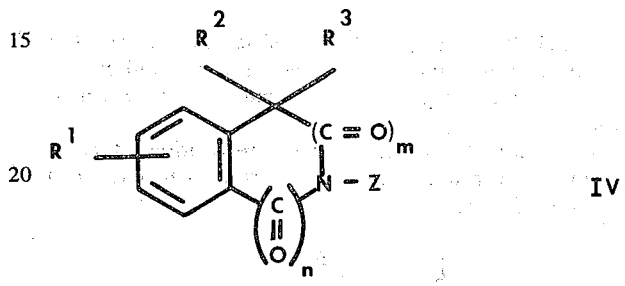

in which $R^1$, $R^2$, $R^3$, m and n are as defined above and Z has the same meaning as

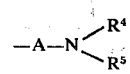

in formula I or signifies a residue, which may be converted into said group, whereafter IV if necessary, is converted into compounds of formula I. As examples of suitable reactive groups Y halogen atoms and arylsulphonyloxy groups can be mentioned.

Examples of groups Z, convertable into the structure

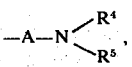

are N-benzyl, N-sulphonyl or N-acyl derivatives of this structure, cyanoalkyl groups, which by hydrogenation after the linking may be transformed into amines or by the addition of water into amides corresponding to formula I, further halogenalkyl, hydroxyalkyl, carboxyalkyl or alkoxykarbonylalkyl radicals, which can be converted into amines respectively amides corresponding to structure I in conventional manner.

Further examples are oxoalkyl radicals, which by reductive amination or via their oxime or hydrazone derivatives can be converted into amines of formula I. If $m = n = 1$, X may also be an oxygen atom, in which case Y in formula III must be a primary amino group. In this case also the corresponding dicarbonic acids can be used instead of the compounds II with $X = 0$.

When $m = 1$, the compounds aimed at can also be obtained by converting a compound of formula

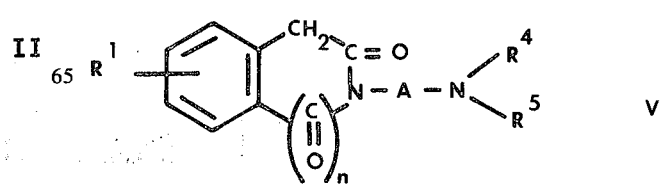

into the desired products by means of dialkylation or cycloalkylation in 4-position.

Alternatively the alkylation may be carried out on a compound of formula VI

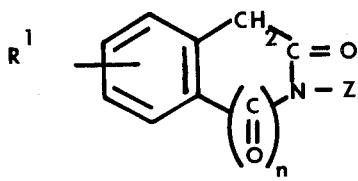

VI in which $R^1$, Z and n are as defined above, and the product of formula IV obtained is converted into a compound corresponding to formula I as described above.

A further alternative for the preparation of compounds of formula I, in which $n = 1$, is to oxidize a compound of formula

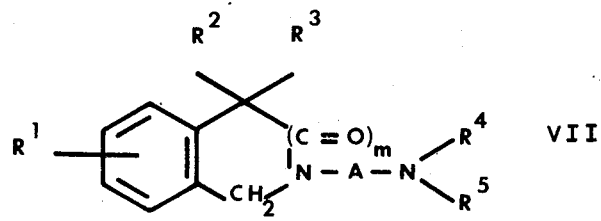

VII in which $R^1$, $R^2$, $R^3$, $R^4$, $R^5$, A and m are as defined above.

The reactions may, of course, also be carried out so as to firstly prepare a lower alkylated amine derivative, a primary amine or a secondary amine, which may then be alkylated in conventional manner to the desired secondary or tertiary amine or quarternary ammonium compound. Similarly, a higher alkylated product can be dealkylated.

Finally, if $R^1$ signifies nitro or halogen, this group can either be present in the starting material or be introduced into the prepared amine of formula I ($R^1 = H$) or at a suitable stage of the reaction series in conventional manner by nitration or halogenation reactions.

The compounds formed can finally, provided that A is not a possibly α-alkylated acetyl group, if desired be converted into salts with physiologically acceptable acids, and the tertiary amines into the corresponding amine oxides.

Starting materials or end products, which are isomer mixtures, may be split into the pure optical antipodes in a manner known per se, for instance by fractionated crystallization of diasterisomeric salts.

The compounds according to the invention have in animal tests proved to possess valuable pharmacological effects, especially on the central nervous system, which are especially manifested as an ability to counteract the effect of reserpine, an effect which in pharmacology is used as a measure of the suitability of a compound as a drug against depressions. The compounds altogether have a low toxicity. Examples of the antireserpine effect of the compounds are given in table I. Certain ones of the compounds at the same time show other effects on the central nervous system, such as a sedative effect as well as antagonism against electroshock.

All experiments were carried out on albino mice, 18 – 25 g. The animals had free access to water except during the test period, but were not allowed to eat 4 – 5 hours before the experiment. The tested substances were administered orally to mice in groups of 6, at 4 dosage levels (12.7; 40; 127 and 400 mg/kg). A control group of 6 mice receiving water was observed simultaneously.

After 1 hour the mice were injected intraperitoneally with 2,5 mg/kg reserpine, which had been solubilized with a few drops of glacial acetic acid. 0.5; 1; and 2 hours after the treatment with reserpine the ptosis was measured; 0 in score is is given for no closure of the eye, 1 for ¼, 2 for ½, 3 for ¾ and 4 for complete closure. The score varies between 0 and 8 for each mouse (the sum of score for 2 eyes). The maximum value for 6 mice is thus 48.

The percentage of antagonism for each compound after 0.5; 1; or 2 hours for each dosage group was obtained by comparision with the score of the simultaneously observed control group. The table indicates the percentage of antagonism after 60 minutes, which is the optimal time for measuring antireserpine effect in this test system.

Table I

| $R^1$ | $R^2$ | $R^3$ | m | n | A | $R^4$ | $R^5$ | Salt | Antagonism % Dosage mg/kg p.o. | | | |
|---|---|---|---|---|---|---|---|---|---|---|---|---|
| | | | | | | | | | 12,7 | 40 | 127 | 400 |
| H | CH₃ | CH₃ | 1 | 1 | —CH₂CO— | H | H | — | | 75 | 96 | 79 |
| H | " | " | 1 | 1 | —CH(C₂H₅CO— | H | H | — | 8 | 46 | 58 | 38 |
| H | " | " | 1 | 1 | —CH₂CH₂— | H | CH₃ | fumarate | | 78 | 94 | |
| H | " | " | 1 | 1 | —CH₂CH₂CH₂— | H | CH₃ | " | 17 | 17 | 92 | |
| H | " | " | 1 | 1 | " | CH₃ | CH₃ | methylsulphate | | 14 | 85 | 55 |
| H | " | " | 1 | 1 | " | CH₃ | CH₃ | perchlorate | 20 | 10 | 70 | |
| H | " | " | 1 | 1 | —CH₂CH₂— | CH₃ | CH₃ | hydrochloride | 46 | 92 | 100 | |
| H | C₂H₅ | C₂H₅ | 0 | 1 | —CH₂CH₂CH₂— | CH₃ | CH₃ | oxalate | | 9 | 27 | 45 |
| H | CH=CHCH₂ | CH₂=CHCH₂ | 1 | 1 | —CH₂CO— | H | H | — | | 10 | 40 | |
| H | —CH₂CH₂CH₂CH₂— | — | 1 | 1 | —CH₂CH₂— | H | CH₃ | fumarate | | 40 | 50 | |
| H | " | " | 1 | 1 | " | CH₃ | CH₃ | sulphate | 75 | 38 | 100 | |
| H | " | " | 1 | 1 | " | CH₃ | CH₃ | methylsulphate | 32 | 53 | 61 | 100 |
| H | " | " | 1 | 1 | " | -N⟨⟩O | | hydrochloride | 38 | 38 | 35 | 91 |
| H | " | " | 1 | 1 | " | -N⟨⟩NH | | diperchlorate | 0 | — | 100 | |
| H | " | " | 1 | 1 | " | C₂H₅ | C₂H₅ | perchlorate | 36 | 45 | 51 | |
| H | " | " | 1 | 1 | —CH(CH₃)CH₂ | CH₃ | CH₃ | " | | | 47 | 84 |
| H | " | " | 1 | 1 | —CH₂CH₂— | CH₃ | CH₃ | N-oxide | | 23 | 69 | 85 |

Table I-continued

| R¹ | R² | R³ | m | n | A | R⁴ | R⁵ | Salt | Antagonism % Dosage mg/kg p.o. 12,7 | 40 | 127 | 400 |
|---|---|---|---|---|---|---|---|---|---|---|---|---|
| H | " |  | 1 | 0 | " | CH₂ | CH₂ | oxalate | 52 | 100 | 100 |  |
| 7-Cl | —CH₂CH₂CH₂CH₂— |  | 1 | 1 | —CH₂CH₂— | CH₃ | CH₃ | fumarate | 27 | 27 | 50 | 45 |
| H | " |  | 1 | 1 | —CH₂CH₂CH₂— | H | CH₃ | hydrochloride |  |  | 100 | 100 |
| H | " |  | 1 | 1 | —CH₂CO— | H | H | — |  | 30 |  | 43 |
| H | " |  | 1 | 1 | —CH₂CH₂CH₂— | CH₃ | CH₃ | perchlorate | 25 | 33 | 42 | 100 |
| H | " |  | 1 | 1 | " | CH₃ | CH₃ | N-oxide | 42 | 42 | 25 | 83 |
| H | " |  | 0 | 1 | " | —N⟨⟩NCH₃ |  | dihydrochloride | 25 | 44 | 44 | 69 |
| H | " |  | 1 | 0 | " | " |  | " | 47 | 47 | 66 | 75 |
| H | —CH₂CH₂CH₂CH₂CH₂— |  | 1 | 1 | " | H | CH₃ | fumarate | 36 | 45 | 100 |  |
| H | " |  | 1 | 0 | " | CH₃ | CH₃ | hydrochloride |  | 25 | 67 | 96 |
| H | " |  | 1 | 1 | " | CH₃ | CH₃ | perchlorate | 42 | 58 | 67 | 90 |
| H | " |  | 0 | 1 | —CH₂CH₂— | CH₃ | CH₃ | hydrochloride | 20 | 40 | 95 |  |
| H | " |  | 1 | 1 | " | —N⟨⟩O |  | free base | 18 | 9 | 45 | 77 |
| H | " |  | 1 | 1 | " | CH₃ | CH₃ | hydrochloride |  | 22 | 72 |  |
| H | —CH₂CH₂CH₂CH₂— |  | 1 | 0 | —CH₂CH₂CH₂— | CH₃ | CH₃ | hydrochloride | 27 | 18 | 63 | 63 |

The following Examples further illustrate the invention.

EXAMPLE 1

4,4-Diallyl-2-(β-dimethylaminoethyl)isoquinoline-1,3-dione 4,4-Diallylhomophtalimide (24.1 g) and N.N-Dimethylaminoethylchloride hydrochloride (14.4 g) in 500 ml of anhydrous dimethylformamide is in portions under agitation mixed with sodium hydride (4.8 g). The mixture is stirred for 3 hours on a boiling water bath, cooled to room temperature and poured on ice. The base formed is extracted with ether. The ether solution is washed with water, dried with anhydrous potassium carbonate and evaporated. 9.4 g of amine are obtained as an oil. This oil is dissolved in anhydrous ether, whereafter a small excess of perchloric acid is added. The precipitated perchlorate is sucked off and crystallized from 2-propanol, after which it forms colour less crystals, m.p. 142°–145°C.

An identical product is obtained if in this example the dimethylformamide is replaced by ethanol and the sodium hydride by potassium carbonate.

In an analogous manner there is obtained:

4,4-Diallyl-2-(γ-dimethylaminopropyl)isoquinoline-1,3-dione, perchlorate, m.p. 126°–128°C.

EXAMPLE 2

2-(4,4-Diallylisoquinoline-1,3-dione)acetamide 4,4-Diallylhomophtalimide (24,1 g) in 500 ml of dimethylformamide is treated with sodium hydride (2,4 g) followed by chloroacetamide (9,3 g) under agitation on a water bath. After 3 hours it is poured on ice and the precipitated solid product is sucked off and crystallized from 2-propanol. M.p. 152.5°–154.5°C. Yield about 80 %.

EXAMPLE 3

3,3-Diethyl-2-β-dimethylaminoethylisoindoline-1-one a. 3,3-Diethylisoindoline-1-one 4,4-Diethylhomophtalimide (13 g) in 180 ml of N sodium hydroxide solution is heated for 60 hours at 60°C, cooled to about 5°C and treated with 65 ml of 1.05 N-sodiumhypochlorite solution. Efter 2 hours it is heated until 60°C for a short while, whereafter the solution is cooled and the precipitated crystalline product is suctioned off. Efter crystallisation from ethanol the product melts at 167°C.

b. 3,3-Diethyl-2-β-dimethylaminoethylisoindoline-1-one 3,3-Diethylisoindoline-1-one (7.55 g), dimethylaminoethylchloride hydrochloride (7.0 g), sodium hydride (2.15 g) and dimethylformamide (150 ml) are heated on a boiling water bath for 4 hours, cooled and poured into water. The separated oil is taken up in ether and dried with solid potassium hydroxide. To the solution obtained an excess of oxalic acid dissolved in ether is added, and crystalline oxalate is precipitated. The salt containing 1 mole of oxalic acid per mole of amine is recrystallized from ethanol and then melts at 159°C. If the ethersolution of the free base is treated with an excess of dimethyl sulphate in ether solution instead of oxalic acid, β-2-(3,3-Diethyl-1-oxoisoindolinyl)ethyl-trimethylammoniummethylsulphate crystallizes, which after crystallization from acetone melts at 180°–185°C.

In an analogous manner there are prepared:

3,3-Diethyl-2-γ-dimethylaminopropylisoindoline-1-one, oxalate, m.p. 137°C after crystallization from acetone.

γ-2-(3,3-Diethyl-1-oxoisoindolinyl)propyltrimethylammoniummethylsulphate, m.p. 161°C.

EXAMPLE 4

2'-[β-Dimethylaminoethylspiro(cyclopentane-1,4'-isoquinoline)]-1,3-dione 1-(2-carboxyphenyl)cyclopentane carbonic acid (23.4 g; 0.100 mole) or the corresponding anhydride (21.6 g) are mixed with β-dimethylaminoethylamine (9.25 g; 0.105 mole) and heated over an open flame until no additional water is removed, after which the product is allowed to cool. The free amine is obtained as an oil. The neutral sulphate containing 2 moles of amine per mole of sulphuric acid crystallizes with one crystal water if the calculated amount of sulphuric acid is added to a solution of the amine in ether and the crude product is isolated and recrystallized from 2-propanol. The salt decomposes at 76° – 86°C.

The perchlorate is obtained in an analogous manner and is crystallized from ethanol, after which it melts at 135° – 137°C.

In an analogous manner there are prepared from the respective dicarboxylic acid or anhydride and a suitable amine component:

4,4-Dimethyl-2-β-methylaminoethylisoquinoline-1,3-dione, monoamine salt with fumaric acid, m.p. 189.5°C.

4,4-Dimethyl-2-β-dimethyl-aminoethylisoquinoline-1,3-dione, hydrochloride, m.p. 176° – 179°C.

4,4-Dimethyl-2-γ-methylaminopropylisoquinoline-1,3-dione, monoamine salt with fumaric acid, m.p. 144° – 147°C.

4,4-Dimethyl-2-γ-dimethylaminopropylisoquinoline-1,3-dione, perchlorate, m.p. 119° – 121°C.

2'-β-Methylaminoethylspiro(cyclopentane-1,4'-isoquinoline)-1',3'-dione, monoamine salt with fumaric acid, m.p. 182°C.

2'-β-Dimethylaminoisopropylspiro(cyclopentane-1,4'-isoquinoline)-1',3'-dione, perchlorate, m.p. 117.5° – 120°C.

2'-β-Diethylaminoethylspiro(cyclopentane-1,4'-isoquinoline)-1',3'-dione, perchlorate, m.p. 152.5 – 155°C.

2'-β-Morpholinoethylspiro(cyclopentane-1,4'-isoquinoline)-1',3'-dione, hydrochloride with one crystal water, m.p. 106° – 115°C.

2'-β-Pyrrolidinoethylspiro(cyclopentane-1,4'-isoquinoline)-1',3'-dione, perchlorate, m.p. 162° – 164.5°C.

2'- (β-1-Piperazinyl)spiro(cyclopentane-1,4'-isoquinoline)-1',3'-dione, diperchlorate, m.p. 237° – 241°C.

2'-(β-4-Methyl-1-piperazinylethyl)spiro(cyclopentane-1,4'-isoquinoline)-1',3'-dione, salt with 2 moles fumaric acid, m.p. 198° – 202°C.

2'-γ-Methylaminopropylspiro(cyclopentane-1,4'-isoquinoline)-1',3'-dione, hydrochloride, m.p. 143.5° – 145.5°C.

2'-γ-Dimethylaminopropylspiro(cyclopentane-1,4'-isoquinoline)-1',3'-dione, perchlorate, m.p. 110° – 117°C.

2'-γ-Diethylaminopropylspiro(cyclopentane-1,4'-isoquinoline)-1',3'-dione, perchlorate, m.p. 137.5° – 140°C.

2'-γ-Cyclohexylaminopropylspiro(cyclopentane-1,4'-isoquinoline)-1',3'-dione, hydrochloride, m.p. 182° – 187°C.

2'-(γ-4-Methyl-1-piperazinylpropyl)spiro(cyclopentane-1,4'-isoquinoline)-1',3'-dione, monoamine salt with 2 moles fumaric acid, m.p. 209.5° – 214.5°C.

2'-β-Dimethylaminoethyl-7'-nitrospiro(cyclopentane-1,4'-isoquinoline)-1',3'-dione, free base, m.p. 113° – 114°C.

2'-γ-Dimethylaminopropyl-7'-nitrospiro(cyclopentane-1,4'-isoquinoline)-1',3'-dione, diamine salt with 1 mole fumaric acid, m.p. 182° – 184.5°C.

2'-β-Dimethylaminoethyl-7'-chlorospiro(cyclopentane-1,4'-isoquinoline)-1',3'-dione, salt with 1 mole fumaric acid, m.p. 159.5° – 164.5°C.

2'-γ-Dimethylaminopropyl-7'-chlorospiro(cyclopentane-1,4'-isoquinoline)-1,3'-dione, salt with 1 mole fumaric acid, m.p. 204.5° – 205.5°C.

2'-γ-Morpholinopropylspiro(cyclopentane-1,4'-isoquinoline)-1',3'-dione, hydrochloride, m.p. 211° – 212°C.

2'-β-Methylaminoethylspiro(cycohexane-1,4'-isoquinoline)-1',3'-dione, monoaminesalt with fumaric acid, m.p. 173.5°C.

2'-β-Dimethylaminoethylspiro(cyclohexane-1,4'-isoquinoline)-1',3'-dione, hydrochloride, m.p. 225.5° – 228°C.

2'-β-Morpholinoethylspiro(cyclohexane-1,4'-isoquinoline)-1',3'-dione, free base, m.p. 82° – 83°C.

2'-γ-Methylaminopropylspiro(cyclohexane-1,4'-isoquinoline)-1',3'-dione, diaminesalt with 1 mole fumaric acid, m.p. 174.5° – 175°C.

2'-γ-Dimethylaminopropylspiro(cyclohexane-1,4'-isoquinoline)-1',3'-dione, picrate, m.p. 186° – 187°C, perchlorate, m.p. 147° – 152°C.

2'-(γ-4-Methyl-1-piperazinylpropyl)spiro(cyclohexane-1,4'-isoquinoline)-1',3'-dione, monoaminesalt with 2 moles fumaric acid, m.p. 212° – 218°C.

2'-β-Dimethylaminoethyl-7'-fluorospiro(cyclopentane-1,4'-isoquinoline)-1',3'-dione. Oil. The perchlorate melts at 174.5° – 182°C.

2'-γ-Dimethylaminopropyl-7'-fluorospiro(cyclopentane-1,4'-isoquinoline)-1',3'-dione. Oil. The perchlorate melts at 96°C.

EXAMPLE 5

2-β-Dimethylaminoethyl-4,4-diethylisoquinoline-1,3-dione a. N-(β-Dimethylaminoethyl)-α-ethyl-α-phenylbutyramide α-Ethyl-α-phenylbutyric acid (38.4 g; 0.2 moles) is refluxed for 3 hours with thionyl chloride (100 ml), whereafter the excess of thionyl chloride is distilled off in vacuum. The oil obtained is dissolved in 100 ml of dioxane and dropwise added to β-Dimethylaminoethylamine (19.4 g; 0.22 moles) in dioxane (300 ml) under agitation. The mixture is allowed to stand for about 12 hours and is diluted with 200 ml of water, whereafter dioxane and water are distilled off in vacuum on a boiling water bath. The mass obtained is dissolved in 2 N hydrochloric acid and washed with ether. The water phase is made alkaline with a 40 % solution of sodium hydroxide and the free base is extracted with ether. After drying with anhydrous potassium carbonate the ether is evaporated and the amine is obtained as a nearly colourless oil in a yield of more than 80 %. The base crystallizes slowly, and a sample recrystallized from diisopropylether melts at 64° – 65°C. In an analogous manner the following intermediates are prepared:

N-(γ-Dimethylaminopropyl)-α-ethyl-α-phenylbutyramide, oil, monoaminesalt with 1 mole fumaric acid, m.p. 127° – 130°C.

N-(β-Dimethylaminoethyl)-α-butyl-α-phenylcapronamide, oil. Hydrochloride, m.p. 193° – 196°C.

N-(γ-Dimethylaminopropyl)-α-butyl-α-phenylcapronamide, oil. Perchlorate, m.p. 125° – 128°C.

N-(β-Dimethylaminoethyl)-1-phenylcyclopentanecarboxamide, oil.

N-(γ-Dimethylaminopropyl)-1-phenylcyclopentanecarboxamide, oil.

N-(β-Dimethylaminoisopropyl)-1-phenylcyclopentanecarboxamide, oil.

N-(β-Dimethylaminoethyl)-1-phenylcyclohexanecarboxamide, oil.

N-(γ-Dimethylaminopropyl)-1-phenylcyclohexanecarboxamide, oil.

N-[γ-(4-Methyl-1-piperazinyl)-propyl]-1-phenylcyclohexanecarboxamide, oil.

b. 2-β-Dimethylaminoethyl-4,4-diethyl-3-oxo 1,2,3,4tetrahydroisoquinoline

A mixture of conc. acetic acid (125 ml), conc. sulphuric acid (25 ml) and paraformaldehyde (7.5 g) are stirred at 50°C until a clear solution is obtained, which is cooled to room temperature. The solution is added to N-β-Dimethylaminoethyl-α-ethyl-α-phenyl-butyramide (32.7 g; 0.125 moles) in portions and heated at 80°C over night, after which it is poured on ice. The solution is washed with ether and the water phase is made alkaline with a 40 % sodium hydroxide solution. The base is extracted with ether and dried with potassium carbonate, after which the ether is evaporated. The amine is obtained as a light yellow oil in an almost quantitative yield. The perchlorate melts at 153.5° – 156°C.

In an analogous manner, the following intermediates are prepared:

2-γ-Dimethylaminopropyl-4,4-diethyl-3-oxo-1,2,3,4-tetrahydroisoquinoline, oil. Monoamine salt with 1 mole citric acid, m.p. 113.5° – 120°C under decomposition.

2-β-Dimethylaminoethyl-4,4-dibutyl-3-oxo-1,2,3,4-tetrahydroisoquinoline, oil. Hydrochloride, m.p. 199.5° – 202°C.

2-γ-Dimethylaminopropyl-4,4-dibutyl-3-oxo-1,2,3,4-tetrahydroisoquinoline, oil. Monoaminesalt with fumaric acid, m.p. 161° – 164.5°C.

2'-β-Dimethylaminoethyl-3'-oxo-1',2',3',4'-tetrahydrospiro(cyclopentane-1,4'-isoquinoline), oil. Boiling point 160° – 165°C/0.2 mm Hg, $n_D^{25}$ = 1.5462. Perchlorate, m.p. 126° – 130°C.

2'-β-Dimethylaminoisopropyl-3'-oxo-1',2',3',4'-tetrahydrospiro(cyclopentane-1,4'-isoquinoline), oil. Boiling point 166° – 169°C/0.1 mm Hg, $n_D^{25}$ = 1.5444. Perchlorate, m.p. 126° – 130°C.

2'-γ-Dimethylaminopropyl-3'-oxo-1',2',3',4'-tetrahydrospiro(cyclopentane-1,4'-isoquinoline), oil. Boiling point 166° – 170°C/0.1 mm Hg, $n_D^{25}$ = 1.5430. Perchlorate, m.p. 126° – 130°C.

2'-β-Dimethylaminoethyl-3'-oxo-1',2',3',4'-tetrahydrospiro(cyclohexane-1,4'-isoquinoline), boiling point 167° – 170°C/0.1 mm Hg, m.p. 80.5° – 84°C.

2'-γ-Dimethylaminopropyl-3'-oxo-1',2',3',4'-tetrahydrospiro(cyclohexane-1,4'-isoquinoline), oil. Boiling point 176° – 180°C/0.1 mm Hg, $n_D^{25}$ = 1.5424.

2'-γ-(4-Methyl-1-piperazinyl)propyl-3'-oxo-1',2',-3',4'-tetrahydrospiro(cyclohexane-1,4'-isoquinoline), oil. Monoamine salt with 2 moles fumaric acid, m.p. 214.5° – 216°C.

c. 2-β-Dimethylaminoethyl-4,4-diethylisoquinoline-1,3-dione

To a solution of 2-β-Dimethylaminoethyl-4,4-diethyl-3-oxo-1,2,3,4-tetrahydroisoquinoline (26.5 g; 0.097 moles) in conc. acetic acid (300 ml) a solution of chromium trioxide (14.5 g) in a mixture of water (30 ml) and conc. acetic acid (180 ml) is added in portions at about 70° – 75°C under agitation. The mixture is kept at this temperature for 4 hours and is allowed to cool over night, after which it is poured on ice and made alkaline with a 40 % solution of sodium hydroxide. The amine is extracted with ether, after which the extract is dried with potassium carbonate and the ether is distilled off. The product is obtained as an almost colourless oil in a yield of more than 90 %. The perchlorate melts at 162° – 164.5°C.

In an analogous manner there are prepared from the above described intermediates:

2-γ-Dimethylaminopropyl-4,4-diethylisoquinoline-1,3-dione, oil. Perchlorate, m.p. 132° – 135°C.

2-β-Dimethylaminoethyl-4,4-dibutylisoquinoline-1,3-dione, oil. Monoamine salt with fumaric acid, m.p. 179.5° – 184.5°C.

2-γ-Dimethylaminopropyl-4,4-dibutylisoquinoline-1,3-dione, oil. Monoamine salt with 1 mole fumaric acid, m.p. 175° – 180°C.

2'-β-Dimethylaminoethylspiro(cyclopentane-1,4'-isoquinoline)-1',3'-dione, oil. Perchlorate, m.p. 135° – 137°C.

2'-β-Dimethylaminoisopropylspiro(cyclopentane-1,4'-isoquinoline)-1',3'-dione, oil. Perchlorate, m.p. 117.5° – 120°C.

2'-γ-Dimethylaminopropylspiro (cyclopentane-1,4'-isoquinoline)-1',3'-dione, oil. Perchlorate, m.p. 110° – 117°C.

2'-β-Dimethylaminoethylspiro(cyclohexane-1,4'-isoquinoline)-1',3'-dione. Oil. Hydrochloride, m.p. 225.5° – 228°C.

2'-γ-Dimethylaminopropylspiro(cyclohexane-1,4'-isoquinoline)-1',3'-dione, oil. Perchlorate, m.p. 147° – 152°C.

2'-(γ-4-Methyl-1-piperazinylpropyl)spiro(cyclohexane-1,4'-isoquinoline)-1',3'-dione, oil. Monoamine salt with 2 moles fumaric acid, m.p. 212° – 218°C.

EXAMPLE 6

2-4,4-Diallylisoquinoline-1,3-dionacetamide

2-Isoquinoline-1,3-dionacetamide(21.8 g; 0.1 mole) in methanol (200 ml) is stirred with anhydrous potassium carbonate (20 g) under reflux boiling while allyl chloride (16.1 g; 0.21 moles) is added dropwise for 30 minutes. The boiling is continued for another 4 hours, after which the major part of the methanol is distilled off. The residue in the flask is treated with water, and a solid product is obtained, which is crystallized from 2-propanol. Colourless crystals of m.p. 152.4° – 154.5°C, identical with the product obtained according to example 2.

In an analogous manner there is obtained with 1,4 - Dibromobutane:

2'-Spiro(cyclopentane-1,4'-isoquinoline)-1',3'-dioneacetamide, m.p. 158° – 161°C.

EXAMPLE 7

2'-β-Dimethylaminoethylspiro(cyclopentane-1,4'-isoquinoline)-1',3'-dione a. 2'-β-Hydroxyethylspiro(cyclopentane-1,4'-isoquinoline)-1',3'-dione A mixture of spirocyclopentane-1,4'-homophtalic acid anhydride (21.6 g; 0.10 moles) and ethanolamine (6.7 g; 0.11 moles) is heated at about 190°C until the development of water steam ceases, after which the product is allowed to cool. Recrystallization from diisopropylic ether yields 24.1 g (93 %) of colourless crystals of m.p. 76° – 77°C.

b. 2'-β-p-Toluenesulfonyloxyethylspiro(cyclopentane-1,4'-isoquinoline)-1,3'-dione The alcohol from (a) (24.1 g; 0.092 moles) is dissolved in pyridine (30 ml) and p-Toluenesulfonylchloride (19.4 g; 0.102 moles) are under agitation added in portions at 10°C for about 30 minutes. The agitation is continued for another 3 hours, after which the mixture is poured on a mixture of 185 g ice and 55.7 ml of conc. hydrochloric acid. The crystalline precipitate is sucked off and washed with ice water, methanol and ether.

After drying, 38 g (98 %) are obtained. A sample is recrystallized from methanol and melts at 98° – 103°C.

c. 2'-β-Dimethylaminoethylspiro(cyclopentane-1,4'-isoquinoline)-1',3'-dione

The tosyl compound from (b) (30 g) is added to a saturated solution of dimethylamine in ethanol (200 ml), after which the solution is kept at room temperature for 7 days in an autoclave. The excess of amine as well as the ethanol are distilled off and the reaction product is treated with water and 1 N sodium hydroxide. The released amine is extracted with ether. After drying with anhydrous potassium carbonate the ether is distilled off and the amine is transformed into crystalline perchlorate of m.p. 135° – 137°C.

EXAMPLE 8

1'-2'-Oxospiro(cyclopentane-1,3'-indoline)acetamide a. 1'-2'-Oxospiro(cyclopentane-1,3'-indoline)acetonitrile 2'-Oxospiro(cyclopentane-1,3'-indoline) (9.4 g; 0.05 moles) is stirred in dimethylformamide (200 ml) with sodium hydride (1.35 g) and chloro acetonitrile (4.4 ml) on a boiling water bath for 4 hours. The mixture is allowed to cool to room temperature, filtered and evaporated to dryness in vacuum. The residue from the evaporation is triturated with water and the product is obtained in a crystalline form in a yield of about 90 %. Crystallization from methanol yields a colourless product of m.p. 109°C.

b. 1'-2'-Oxospiro(cyclopentane-1,3'-indoline)acetamide

The corresponding nitrile (2.0 g) is added to 10 ml of ice-cold 93 % sulphuric acid. The mixture is kept at 0°C for 4 hours and poured on ice, upon which the amide crystallizes. Recrystallization from aceton with ether yields a colourless product of m.p. 119° – 121°C.

EXAMPLE 9

2'-β-Aminoethylspiro(cyclopentane-1,4'-isoquinoline)-1,3'-dione a. 2'-α-Diethoxymethylspiro(cyclopentane-1,4'-isoquinoline)-1',3'-dione To spiro(cyclpentane-1,4'-isoquinoline)-1',3'-dione (43 g; 0.2 moles) in 500 ml of dimethylformamide there is added under agitation sodium hydride (50 % suspension in oil; 11.5 g; 0.24 moles). After the vivid development of hydrogen gas has ceased chloroacetaldehyde diethylacetal (36.5 g; 0.24 moles) is added and the mixtures are refluxed for 3 days and cooled. After dilution with 500 ml of water the acetal formed is extracted with ether. After drying with potassium carbonate and evaporation of the ether there are obtained 58.1 g of an oil, which soon crystallizes. Yield 87.5 %. A sample is recrystallized from n-hexane and melts already at 65.5° – 67°C.

b. 2'-α-Formylmethylspiro(cyclopentane-1,4'-isoquinoline) -1',3'-dione

The above acetal (48 g; 0.145 moles) is refluxed for 12 hours with 400 mls of 2 N hydrochloric acid and cooled. The crystalline product is sucked off, washed with water and crystallized from n-hexane. Yield 35.9 g (96.2 %). M.p. 75.5° – 77.5°C.

c. 2'-β-Oximinoethylspiro(cyclopentane-1,4'-isoquinoline)-1',3'-dione

The above aldehyde (12.85 g; 0.05 moles), 2 N sodium hydroxide solution (37.5 mls), hydroxylamine hydrochloride (5.2 g; 0.075 moles) and ethanol (100 mls) are refluxed for 12 hours. The ethanol is distilled off and water is added to the oil suspension obtained. Upon cooling the oxime crystallizes, is sucked off and washed with water. Yield 13.5 g (98.5 %). After crystallization from diisopropylether the product melts at 111° – 115°C.

d. 2'-β-Aminoethylspiro(cyclopentane-1,4'-isoquinoline)-1',3'-dione

The oxime (6.4 g; 0.024 moles) in 350 mls of ethanol containing 10 g of hydrogen chloride is reduced at atmospheric pressure and room temperature with 400 mg of platina oxide as a catalyst. The reaction is completed after about 3 hours. The catalyst is filtered off and the solution is concentrated in vacuum on a water bath of 30°C. The hydrochloride is obtained as an oil, which soon crystallizes. Crystallization from 2-propanol yields 3.5 g of hydrochloride having the m.p. 203° – 207°C.

In an analogous manner there is produced:

2'-γ-Aminopropylspiro)cyclopentane-1,4'-isoquinoline)-1',3'-dione with the melting point 64° – 67.5°C. The perchlorate melts at 254.5° – 256.5°C.

EXAMPLE 10

2'-Spiro(cyclopentane-1,4'-isoquinoline)-1',3'-dioneacetamide a. 2'-Spiro(cyclopentane-1,4'-isoquinoline)-1',3'-dioneacetonitrile Spirocyclopentanehomophtalic acid anhydride (11.7 g) in ether (50 ml) is added to a solution of aminoacetonitrile (5.6 g) in ether (400 ml). The ether is distilled off and the evaporation residue is heated over an open flame until no more water is removed. The temperature in the melt is then about 190°C. The product is crystallized from diisopropylether and melts thereafter at 87.5° – 89.5°C. Yield about 80 %.

b. 2-Spiro(cyclopentane-1,4'-isoquinoline)-1',3'λ dioneacetamide

This compound is obtained if the nitrile is treated with sulphuric acid as described in example 8. After crystallization from 2-propanol the product melts at 158° – 161°C.

EXAMPLE 11

2-β-Dimethylaminoethyl-4,4-dipropargylisoquinoline-1,3-dione a. 4,4-Dipropargylhomophtalimide Propargyl bromide (172 g; 1.44 ml) is under agitation dropped to a solution of homophtalimide (116.3 g; 0.72 moles) in water (150 ml) containing sodium hydroxide (57.6 g). The mixture is triturated over water in a boiling water bath. After cooling to room temperature the product is sucked off and crystallized from acetic acid. M.p. 219.5° – 220°C.

b. 2-β-Dimethylaminoethyl-4,4-dipropargylisoquinoline-1,3-dione

Sodium hydride, 50 % suspension in oil (9.6 g) is added in portions under agitation to a mixture of 4,4-Dipropargylhomophtalimide (23.7 g; 0.1 moles), β-dimethylaminoethylchloride hydrochloride (14.4 g; 0.1 moles) and dimethylformamide (500 ml) at room temperature. The mixture is triturated with water in a boiling water bath, cooled and poured into ice water. The amine is extracted with ether. The ether phase is washed with water and extracted three times with 2 N hydrochloric acid. The hydrochloric acid phase is washed with ether and made strongly alkaline, after which the released amine is taken up in ether and dried with solid sodium carbonate. Evaporation of the compound yields an oil (24.0 g; 78 % yield). The perchlorate is obtained if an excess of perchloric acid is added to a solution of the amine in ether. After crystallization from 2-propanol the product melts at 160°C.

EXAMPLE 12

2'-Spiro(cyclopentane-1,4'-isoquinoline)-1',3'-dioneacetamide

Spirocyclopentanehomophtalimide (21.5 g; 0.1 mole) is stirred in dimethylformamide (150 ml) with sodium hydride (2.4 g) until the development of hydrogen ceases. A solution of α-hydroxyacetamide p-toluene sulphonic acid ether (23 g; 0.1 mole) is added and the mixture is stirred on a water bath for 6 hours. The major part of the solvent is distilled off in vacuum and the residue in the flask is treated with water, upon which the amide crystallizes slowly. The product is identical with the one obtained according to example 10.

EXAMPLE 13

1'-β-Aminoethylspiro)cyclopentane-1,3'-indoline)-2'-one

1'-2'-Oxospiro(cyclopentane-1,3'-indoline)acetonitrile (7.5 g) in ethanol (100 ml) and conc. ammonia solution (25 ml) are hydrogenated at 3 kg/cm$^2$ for 5 hours with a Raney-nickel catalyst. The catalyst is filtered off and the filtrate evaporated in vacuum, the amine being obtained as a colourless oil. This gives a crystalline oxalate which decomposes at 160°C.

EXAMPLE 14

1'-β-Methylaminoethylspiro(cyclopentane-1,3'-indoline)-2'-one a. 1'-β-p-Toluenesulphonamidoethylspiro(cyclopentane-1,3'-indoline)-2'-one The free amine (7.0 g), p-toluenesulphochloride (6.9 g) and a solution of 2 N sodium hydroxide (37 ml) are mixed and stirred for about 30 minutes on a water bath under moderate heating. The mixture is kept at room temperature for about 18 hours. The solid mass is triturated and the crystalline product is sucked off, washed and crystallized from ethanol, upon which 10 g (85 %) of a crystalline product of m.p. 60°C is obtained.

b. 1'-β-N-Methyl-N-p-toluenesulphonylamidoethyl-spiro(cyclopentane-1,3'-indoline)-2'-one The tosyl derivative from example 14(a) (9.8 g) is stirred with sodium hydride (0.7 g), anhydrous benzene (100 ml) and dimethylformamide (25 ml). Methyliodide (19 ml) is added drop-wise under heating on a water bath for 2 hours. The solution is evaporated in vacuum and the evaporation residue is treated with water and ether. The ether extract is washed with a diluted solution of sodium hydroxide and evaporated. The solid product crystallizes from ethanol and then melts at 107°C.

c. 1'-β-N-Methylaminoethylspiro(cyclopentane-1,3'-isoindoline)-2'-one -N-Methylaminoethylspiro(cyclopentane-1,3

The tosyl derivative from example 14 (b) (3.2 g is refluxed for 72 hours with a mixture of conc. hydrochloric acid (15 ml) and conc. acetic acid (20 ml). The solution is evaporated and the oil thus obtained is triturated with ethanol and petroleum ether, upon which a crystalline product is obtained. Recrysallization from ethanol-ether yields a colourless hydrochloride of m.p. 236°C.

EXAMPLE 15

1'-1-β-N-Methylaminoethylpiro(cyclopentane-1,31'-indoline)- 2'-one a. 1'-β-N-Benzyl-N-methylaminoethylspiro(cyclopentane1,3'-indoline)-2'-one A mixture of spirocyclopentane indoline-2-one (4.7 g), sodium hydride (1.35 g), β-N-Benzyl-N-methylaminoethylchloride (6.6 g) and dimethylformamide (100 ml) is stirred on a water bath for 3.5 hours, after which the solvent is distilled off in vacuum. The remaining mass is triturated with water and the oily product is extracted with ether. After drying with potassium carbonate the ether is removed, and 6.8 g (81.5 %) of an oil is obtained. A sample is converted into the oxalate, which after reprecipitation from ethanol with ether forms colourless crystals, containing 1 mole of crystal water and decomposing at 90° – 100°C.

b. 1'-β-N-Methylaminoethylspiro(cyclopentane-1,3'-isoindoline)-2'-one

The benzyl derivative from example 15(a) (2.5 g) in acetic acid(25 ml) is hydrogenated at 4 kg/cm$^2$ for 30 hours at room temperature with 10 % palladium on coal as a catalyst (0.5 g). The catalyst is filtered off and the filtrate is evaporated in vacuum. The product is treated with ether and hydrogen chloride and the salt crystallizes from ethanol. The hydrochloride melts at 236°C and is identical with the product obtained according to example 14.

EXAMPLE 16

2'-(β-4-Methyl-1-piperazinylethyl)spiro(cyclopentane-1,4'isoquinoline)-1',3'-dione 2'-(β-piperazinylethyl)spiro(cyclopentane-1,4'-isoquinoline)-1', 3'-dione (32.1 g), formic acid (25 g) and a 37 % formaldehyde solution (22.5 ml) are mixed and refluxed for 8 hours. After cooling a mixture of conc. hydrochloric acid (50 ml) and water (50 ml) is added, after which the solution is evaporated to dryness in vacuum on a water bath. The salt residue is dissolved in a small amount of water and made alkaline with a 50 % solution of sodium hydroxide. The free base is extracted with ether, dried with potassium carbonate and evaporated, upon which 12.6 g of an oil are obtained. The salt with 2 moles fumaric acid melts at 198° – 202°C.

EXAMPLE 17

2-(4,4-Dimethylisoquinoline-1,3-dione)-α-ethylacetamide a. 2-(4,4-Dimethylisoquinoline-1,3-dione)-α-ethylacetic acid 4,4-Dimethylhomophtalic anhydride (41.6 g; 0.2 moles), α-Aminobutyric acid (20.6 g; 0.2 moles) are mixed intimately and heated until no more water is removed. The melt is allowed to cool, and the product is crystallized from acetic acid - water Yield 77 %, m.p. 107 - 110°C.

In an analogous manner there is prepared
2-(4,4-Dimethylisoquinoline-1,3-dione)acetic acid, melting point 146° – 149°C.

b. 2-(4,4-Dimethyl-α-isoquinoline-1,3-dione)-α-ethylacetamide

The acid from example 17 (a) (22.1 g 0.08 moles), thionyl chloride (11.9 g; 0.10 moles), methylene chloride (50 ml) and a drop of dimethylformamide are refluxed for 0.5 hours and evaporated in vacuum, after which the product is again dissolved in methylene chloride and poured under agitation to a mixture of a solution of conc. ammonia and ice. After 1 hour the product is sucked off, washed and crystallized from diluted ethanol. M.p. 138° – 140°C.

In an analogous manner there are prepared:

2-(4,4-Dimethylisoquinoline- 1,3-dione)acetamide, m.p. 174 - 177°C.

2'-[7'-Chlorospiro(cyclopentane-1',4'-isoquinoline)-1',3'-dione]-acetamide. Crystals from ethanol. M.p. 167° – 172°C.

EXAMPLE 18

2'-Spiro(cyclopentane-1,4'-isoquinoline)-1',3'-dioneacetamide

Spirocyclopentane homophtalic acid (23.4 g; 0.1 mole) and glycine (7.5 g; 0.1 mole) are mixed intimately and heated to about 190°C until the removal of water ceases. After cooling, thionyl chloride (100 ml) is added and the mixture is refluxed for 1 hour, after which the excess of thionyl chloride is distilled off. The crude acid chloride is dissolved in 100 ml of dioxane and under agitation dropwise added to a solution of 250 ml of conc. ammonia under cooling with ice. The product is sucked off and crystallized from 2-propanol. M.p. 158° – 161°C.

In an analogous manner there are produced:

7'-Nitrospiro(cyclopentane-1,4'-isoquinoline)-1',3'-dioneacetamide, m.p. 208.5° – 211°C. 7'-Chlorospiro(-cyclopentane-1,4'-isoquinoline)-1',3'-dioneacetamide, m.p. 167° – 172°C.

EXAMPLE 19

1'-Spiro(cyclopentane-1,3'-indoline)-2'-oneacetamide a. 1-Spiro(cyclopentane-1,3'-indoline)-2'-oneacetic acid ethylester Spirocyclopentane indoline-2-one (7.5 g), sodium hydride (1.0 g) and dimethylformamide (200 ml) are stirred on a water bath for 0.5 hours, after which ethylchloroacetate (13 g) is added. The mixture is heated and stirred for another 5 hours, whereafter the major part of the solvent is distilled off in vacuum and the residue in the flask is treated with water. The oil thus obtained crystallizes when triturated. The product is recrystallized from aceton and melts at 89°C. Yield 85 %.

In an analogous manner there is obtained from 2'-Spiro-(cyclopentane-1,3'-isoindoline)-1'-one:

2'-Spiro(cyclopentane-1,3'-isoindoline)-1'-oneacetic acid ethyl ester, as an oil.

b. 1'-Spiro(cyclopentane-1,3'-indoline)-2'-oneacetamide

The ethyl ester from example 19 (a) (7.9 g) in 50 ml methanol is added to 40 ml of liquid ammonia and the mixture is kept at room temperature for 5 days in an autoclave. The ammonia is allowed to evaporate and water is added to the methanolic solution thus obtained, upon which the product crystallizes. Recrystallization from a mixture of 15 ml aceton, 10 ml ether and 5 ml petroleum ether yields 3.5 g of a colourless product of m.p. 119° – 121°C.

In an analogous manner there is obtained:

2'-Spiro(cyclopentane-1,3'-isoindoline)-1''-oneacetamide of m.p. 144° –150°C.

EXAMPLE 20

2'-Spiro(cyclopentane-1,3'-isoindoline)-1'-oneacetamide

Spirocyclopentane isoindoline-2'-one (9.5 g; 0.05 moles), sodium hydride (1.3 g), dimethylformamide (200 ml) and chloroacetamide (5.6 g; 0.06 moles) are stirred at room temperature over night and evaporated to dryness in vacuum. The evaporation residue is treated with acetone, unsolved salt is filtered off and the acetone is driven off from the filtrate. An oil is obtained which crystallizes when triturated. The product is identical with the material obtained according to example 19.

EXAMPLE 21

1'-γ-Dimethylaminopropylspiro(cyclopentane-1,3'-indoline)-2'-one a. 1'-γ-Chloropropylspiro(cyclopentane-1,3'-indoline)-2'-one Sprio(cyclopentane-1,3'-indoline)- 2'-one (7.5 g), sodium hydride (1.2 g), dimethylformamide (200 ml) are stirred at room temperature until the hydride has been consumed. The solution obtained is added dropwise under-agitation to a solution of 1-bromo-3-chloropropane (12.1 g) in 25 ml of dimethylformamide. The mixture is stirred for about 18 hours on a water bath, after which the solvent is distilled off in vacuum. The residue from the distillation is treated with water and the oil obtained is extracted with ether and dried with potassium carbonate, whereafter the ether is driven off. The chloride is obtained as a brown oil.

b. 1'-γ-Dimethylaminopropylspiro(cyclopentane-1,3'-indoline)-2'-one

The crude chloride from a) is heated at 120°C with a solution of dimethylamine (20 g) in toluene (100 ml) for 4 hours. The excess of dimethylamine is distilled off and the toluene solution obtained is extracted with 2 N hydrochloric acid. The hydrochloric acid extract is washed with ether, made alkaline and again extracted with ether. The ether phase is dried over solid potassium hydroxide and a solution of gaseous hydrogen chloride in ether is added as long as precipitation occurs. The product crystallizes upon triturated, is sucked off and recrystallized from a mixture of ethanol and ether. M.p. 173°C.

In an analogous manner there are obtained:

1'-γ-Methylaminopropylspiro(cyclopentane-1,3'-indoline)- 2'-one. Oil. Monoamine salt with 1 mole oxalic acid, m.p. 179 °C.

3,3-Diallyl-1-β-dimethylaminoethylindoline-2-one, salt with 1 mole oxalic acid and 1 mole of hydrate water. M.p. 133° – 137°C.

3,3-Diallyl-1-γ-dimethylaminopropylindoline-2-one, salt with 1 mole of oxalic acid, m.p. 130°C.

3,3-Diallyl-2-β-dimethylaminoethylisoindoline-1-one, salt with 1 mole of oxalic acid, m.p. 149° – 151°C.

3,3-Diallyl-2-γ-dimethylaminopropylisoindoline-1-one, salt with 1 mole of oxalic acid, m.p. 166°C.

1'-γ-Dimethylaminopropyl-6'-chlorospiro(cyclopentane-1,3'-indoline)-2'-one, salt with 1 mole of oxalic acid, m.p. 173° – 176°C.

1'-β-Dimethylaminoethylspiro(cyclohexane-1,3'-indoline)-2'-one, salt with 1 mole of oxalic acid, m.p. 165° – 166°C.

1'-β-Dimethylaminoethyl-6'-nitrospiro(cyclopentane-1,3'-indoline)-2'-one. Free base. M.p. 74° – 75°C.

1'-γ-Dimethylaminopropyl-6'-nitrospiro(cyclopentane-1,3'-indoline)-2'-one, salt with 1 mole of oxalic acid. M.p. 172° – 174°C. 1'-β-Dimethylaminoethyl-6'-fluorospiro(cyclopentane-1,3'indoline)-2'-one, salt with 1 mole of oxalic acid. M.p. 169° – 171°C.

1'-γ-Dimethylaminopropyl-6'-fluorospiro(cyclopentane-1,3'-indoline)-2'-one, salt wih 1 mole oxalic acid. M.p. 169° – 170°C.

EXAMPLE 22

2'-β-Dimethylaminoethylspiro(cyclopentane-1,3'-isoindoline)-1'-one a. Spiro(cyclopentane-1,3'-isoindoline)-1'-one Spiro(cyclopentane-1,4'-homophtalimide) (6.5 g) in 60 ml 2 N solution of sodium hydroxyd is kept at room temperature for 20 days. A 1.08 molar solution of sodium hypochlorite (32 ml) is added. After 2 hours there is heated to 60°C for 15 minutes and cooled, after which the crystalline product is filtered off and crystallized from ethanol-water. The product melts at 177°C.

b. 2'-β-Dimethylaminoethylspiro(cyclopentane-1,3'-isoindoline)-1'-one

Spiro(cyclopentane-1,3'-isoindoline)-1'-one (9.4 g; 0.05 moles), sodium hydride (2.65 g; 0.11 moles), β-Dimethylaminoethylchloride hydrochloride (8.7 g; 0.06 moles) and dimethylformamide (200 ml) is stirred under heating on a water bath for 18 hours. The major part of the solvent is distilled off in vacuum and water is added to the distillation residue. The solution is washed with ether and made strongly alkaline with a solution of sodium hydroxide, after which the free base is extracted with ether. The extract is dried with solid potassium hydroxide and evaporated, and the base is obtained as an oil. The latter (2.2 g) is dissolved in 50 ml of ether, whereafter a solution of oxalic acid (1.1 g) in 2.5 ml of methanol and 7.5 ml ether is added. White crystals (3.0 g) of m.p. 138°C are obtained The salt is a sesquioxalate with 1.5 moles of oxalic acid/mole of base.

In an analogous manner there are obtained:

2'-γ-Dimethylaminopropylspiro(cyclopentane-1,3'-isoindoline)-1'-one, salt with 1 mole of oxalic acid, m.p. 117°C.

2'-(γ-Dimethylamino-β-methylpropyl)spiro(cyclopentane-1,3'-isoindoline)-1'-one, salt with 1 mole of oxalic acid, m.p. 139°C.

2'-γ-(4-Methyl-1-piperazinyl)propylspiro(cyclopentane-1,3'-isoindoline)-1'-one, dihydrochloride, m.p. about 205°C under decomposition.

2'-β-Dimethylaminopropylspiro(cyclopentane-1,3'-isoindoline)-1'-one, sesquioxalate, m.p. 138°C.

2'-β-N-Benzyl-N-methylaminoethylspiro(cyclopentane-1,3'-isoindoline)-1'-one, oxalate with 1 mole of crystal water, m.p. 155° – 158°C.

EXAMPLE 23

2'-β-Methylaminoethylspiro(cyclopentane-1,3'-isoindoline)-1'-one

The N-benzyl derivative from example 22 (6.5 g) in acetic acid (50 ml) is hydrogenated for 24 hours at room temperature at about 4 kg/cm² with hydrogen in the presence of 1.0 g of 10 % palladium-coal catalyst. After filtration the acetic acid is evaporated in vacuum, the product is poured into water, made alkaline and taken up in chloroform. After drying with sodium sulphate the solution is evaporated, upon which 4.3 g of the amine are obtained as an oil. The latter is dissolved in somewhat acetone and treated with the solution of 1.53 g oxalic acid in ether. The sesquioxalate crystallizes as colourless crystals, which after recrystallization from acetone melt at 155° – 160°C.

EXAMPLE 24

2'-β-Dimethylaminoethylspiro(cyclohexane-1,3'-isoindoline)-1'-one a. Spiro(cyclohexane-1,1'-isoquinoline)-3'-4'-dione Spiro(cyclohexane-1,1'-isoquinoline)-3'-one (12.9 g; 0.06 moles) in acetic acid anhydride (20 ml) is oxidized with selenium dioxide (10 g; 0.09 moles) under reflux for 3 hours. After dilution with acetic acid (20 ml) the precipitated selenium is filtered off the boiling hot solution and the filtrate is cooled. The crystalline product is filtered off and washed with acetic acid and water. Yield 6.8 g of pale yellow crystals of m.p. 180°C. Recrystallization from ethanol increases the melting point to 189° – 192°C.

b. Spiro(cyclohexane-1,3'-isoindoline)-1'-one

The product from example 24 (a) (11.5 g; 0.05 moles) is dissolved in hot ethanol (100 ml.) A solution of sodium hydroxide (10 ml), 40 %, is added, followed under agitation by 30 % hydrogenperoxide (50 ml) in portions for about 20 minutes. The light yellow solution is heated and stirred for another 20 minutes and allowed to cool, after which the crystalline product is filtered off and recrystallized from ethanol. Yield 4.0 g, m.p. 232° – 234°C.

c. 2'-β-Dimethylaminoethylspiro(cyclohexane-1,3'-isoindoline)-1'-one

This product is obtained when the spirocyclohexane isoindolinone from example 24 (b) is treated analogously with example 22. The hydrochloride melts at 245°C.

In an analogous manner there is obtained:

2'-γ-Dimethylaminopropylspiro(cyclohexane-1,3'-isoindoline)-1'-one. Monoamine salt with 1 mole of oxalic acid and 1 mole of crystal water, m.p. 150° – 160°C.

EXAMPLE 25

β-2-(4,4-Dimethyl-1,3-dioxo-1,2,3,4-tetrahydroisoquinolinyl)-ethyltrimethylammoniummethylsulphate To the corresponding tertiary amine (6.5 g) in ether (250 ml) dimethylsulphate (6.5 ml) is added. The crystalline product is filtered off and recrystallized from ethanol, m.p. 208.5° – 211°C.

In an analogous manner there are obtained:

γ-2-(4,4-Dimethyl-1,3-dioxo-1,2,3,4-tetrahydroisoquinolinyl)propyltrimethylammoniummethylsulphate, m.p. 175° –178°C.

β-2'-[1',3'-Dioxo-1',2',3',4'-tetrahydrospiro(cyclohexane-1,4'-isoquinolinyl)]-ethyltrimethylammoniummethylsulphate, m.p. 192°C.

γ-2'-[1',3'-Dioxo-1',2',3',4'-tetrahydrospiro(cyclopentane-1,4'-isoquinolinyl)]-propyltrimethylammoniummethylsulphate, m.p. 212° – 214°C.

β-2'-[1',3'-Dioxo-1',2',3',4'-tetrahydrospiro(cyclopentane-1,4'-isoquinolinyl)]-ethyltrimethylammoniummethylsulphate, m.p. 198° – 201°C.

N-β-2'-[1',3'-Dioxo-1',2',3',4'-tetrahydrospiro(cyclopentane-1,4'-isoquinolinyl)]-ethyl-N,N-diethyl-N-methylammoniummethylsulfate m.p. 155° – 158.5°C.

N-β-2'-[1',3'-Dioxo-1',2',3',4'-tetrahydrospiro(cyclopentane-1,4'-isoquinolinyl)]-ethyl-N-methylmorpholiniummethylsulphate, m.p. 171° – 180°C.

β-2'-[1'-Oxospiro(cyclopentane-1,3'-isoindolinyl)]-ethyltrimethylammoniummethylsulphate. Decomposes vaguely at about 158°C.

γ-2'-[1'-Oxospiro(cyclopentane-1,3'-isoindolinyl)]-propyltrimethylammoniummethylsulphate, m.p. 168°C.

β-2'-[1'-Oxospiro(cyclohexane-1',3'-isoindolinyl)-]ethyltrimethylammoniummethylsulphate, m.p. 230° – 240°C.

γ-2'-[1'-Oxospiro(cyclohexane-1,3'-isoindolinyl)]-propyltrimmethylammoniummethylsulphate, m.p. 226°C.

β-1'-[2'-Oxospiro(cyclopentane-1,3'-indolinyl)]ethyltrimethylammoniummethylsulphate, m.p. 166°C.

γ-1'-[2'-Oxospiro(cyclopentane-1,3'-indolinyl)]-propyltrimethylammoniummethylsulphate, m.p. 210°C.

β-1-(3,3-Dimethyl-2-oxoindolinyl)ethyltrimethylammoniummethylsulphate, m.p. 158°C.

γ-1-(3,3-Dimethyl-2-oxoindolinyl)propyltrimethylammoniummethylsulphate, m.p. 170°C.

N-γ-2'-[1',3'-Dioxo-1',2',3',4'-tetrahydrospiro(cyclohexane-1,4'-isoquinolinyl)]-propyl-trimethylammoniummethylsulphate, m.p. 150°.

EXAMPLE 26

N-N-Dimethyl-2'-[1',3'-dioxo-1',2',3',4'-tetrahydrospiro-(cyclopentane-1,4'-isoquinolinyl)]ethylamine oxide N,N-Dimethyl-2'-[1',3'-Dioxo-1',2',3',4'-tetrahydrospiro-(cyclopentane-1,4'-isoquinolinyl)]-ethylamine (6 g; 0.021 moles) is dissolved in 10 ml of ethanol, after which 30 % hydrogen peroxide (2.14 ml) are added. After 2 days at room temperature the methanol is distilled off in vacuum on a water bath and the product is crystallized from acetone with an addition of diisopropylic ether. Yield 90 %, m.p. 56° – 58°C.

In an analogous manner there are obtained from the respective tertiary amines:

N,N-Dimethyl-2'-[1',3'-dioxo-1',2',3',4'-tetrahydrospiro-(cyclopentane-1,4'-isoquinolinyl)]propylamine oxide. Crystals with 3 moles of crystal water, m.p. 137.5° – 139°C.

N,N-Dimethyl-1'-[2'-oxospiro(cyclopentane-1,3'-indolinyl)]ethylamine oxide. Crystals with 1 mole of crystal water, decompose at 100° – 110°C.

N,N-Dimethyl-1'-[2'-oxospiro(cyclopentane-1,3'-indolinyl)]propylamine oxide. Viscous oil.

EXAMPLE 27

1-β-Dimethylaminoethyl-3,3-dimethylindoline-2-one 3,3-Dimethylindoline-2-one (8,1 g; 0.05 moles) in 200 ml of dimethylformamide is treated with sodium hydride (2.65 g; 0.11 moles) and dimethylamino ethylchloride hydrochloride (8.7 g; 0.06 moles) under agitation on a water bath for 18 hours. The major part of the solvent is distilled off in vacuum and the distillation residue is dissolved in water, washed with ether, made strongly alkaline with a solution of sodium hydroxide and extracted with ether. The extracts are dried with solid potassium hydroxide and evaporated, after which the amine is obtained in the form of an oil. This is dissolved in ether and treated with oxalic acid dissolved in ether, upon which the monoamine salt with 1 mole of oxalic acid crystallizes. After recrystallization from a mixture of acetone-methanol the product melts at 175°C.

In an analogous manner there are prepared:

1-γ-Dimethylaminopropyl-3,3-dimethylindoline-2-one. Monoamine salt with 1 mole of oxalic acid, m.p. 139° – 141.5°C.

1'-β-Dimethylaminoethyl-2'-oxospiro(cyclopentane-1,3'-indoline). Salt with 1 mole of oxalic acid, m.p. 168°C.

1'-γ-Dimethylaminopropyl-2'-oxospiro(cyclopentane-1,3'-indoline). Hydrochloride, m.p. 173°C.

1'-β-Dimethylaminopropyl-2'-oxospiro(cyclopentane-1,3'-indoline). Hydrochloride, m.p. 175° – 180°C.

1'-(γ-Dimethylamino-β-methylpropyl-2'-oxospiro(-cyclopentane-1,3'-indoline). Monoamine salt with oxalic acid, m.p. 140° – 145°C.

1'-γ-(4-Methyl-1-piperazinyl)propyl-2'-oxospiro(cyclopentane-1,3'-indoline). Dihydrochloride, m.p. 210°C.

1'-γ-Dimethylaminopropyl-2'-oxospiro(cyclohexane-1,3'-indoline). Hydrochloride, m.p. 181°C.

EXAMPLE 28

1'-β-Dimethylaminoethyl-6'-chloro-2'-oxospiro(cyclopentane-1,3'-indoline)

is obtained if in ex 27 the spirocyclopentane indolinone is replaced by 6'-chlorospiro(cyclopentane-1,3'-indoline)-2'-one. The amine is obtained as an oil. The hydrochloride is obtained if a solution of the amine in ether is treated with anhydrous hydrogenchloride. Crystallization from aceton yields colourless crystals of m.p. 249°C. The chloroindolinone used as starting material forms dimorphous crystals of m.p. 128°C and 144°C.

EXAMPLE 29

1'-Dimethylaminoethyl-5'-chlorospiro(cyclopentane-1,3'-indoline)-2'-one a. 5'-Chlorospiro(cyclopentane-1,3'-indoline)-2-one
Spiro(cyclopentane-1,3'-indoline)-2'-one (18,7 g; 0.10 moles) is dissolved in acetic acid (50 ml) containing 100 mg of ferricloride hexahydrate, cooled in ice-water and drop-wise treated under agitation with a solution of clorine in acetic acid (82 ml of a solution containing 7,8 g per 100 ml). After the addition air is blown through the solution to eliminate a possible excess of clorine as well as hydrogen cloride. The crystallized product (8.7 g) is sucked off and the filtrate is concentrated in vacuum, upon which an additional product quantity (7.3 g) is obtained. After recrystallization from ethanol the substance melts at 201° – 202°C.

If an excess of clorine is used in this example there is obtained 5',7'-Dichlorospiro(cyclopentane-1,3'-indoline)-2'-one of m.p. 175° – 176°C.

b. 1'-β-Dimethylaminoethyl-5'-chlorospiro(cyclopentane-1,3'-indoline)-2'-one
5'-Chlorospiro(cyclopentane-1,3'-indoline)-2'-one is reacted with β-Dimethylaminoethylchloride as described in example 1. The free base melts at 69° – 70°C.
In an analogous manner there are prepared 1'-γ-Dimethylaminopropyl-5'-chlorospiro(cyclopentane-1,3'-indoline)-2'-one. Salt with 1 mole of oxalic acid, m.p. 158° – 159°C.

1'-β-Dimethylaminoethyl-5',7'-dichlorospiro(cyclopentane-1,3'-indoline)-2'-one. Salt with 1 mole of oxalic acid, m.p. 163° – 164°C.

1'-γ-Dimethylaminopropyl-5'-7'-dichlorospiro(cyclopentane-1,3'-indoline)-2'-one. Hydrochloride m.p. 253° – 254°C.

EXAMPLE 30

2'-β-Dimethylaminoethyl-4-oxospiro(cyclohexane-1,4'-isoquinoline)-1',3'-dione.

Homophtalicacid anhydride (137 g; 0.85 mole), β-dimethylaminoethylamine (76,5 g; 0.87 mole) and xylene (400 ml) are boiled with continued separation of the water formed until a homogeneous solution is obtained and no additional water is formed. The xylene is distilled off in vacuum on a waterbath and the oil obtained is dissolved in 2 l of ether. Unsolved solid material is filtered off and the ether is distilled off. 175 g of crude 2-β-Dimethylaminoethylhomophtalimide is then obtained. Finely divided potassium carbonate (262 g; 1,9 mole) is added to the crude product (110 g 0.474 mole) in 2 l of dimethylformamide and the mixture is heated to 110°C. 1,5-Dichloropentane-3-one (73.5 g; 0.474 mole) is added drop drop-wise under vigorous agitation. After this addition which lasts for 1.5 hours, the mixture is heated for another 2 hours and then poured into 6 l of water. The solution is extracted three times with chloroform. The combined chloroform extracts are washed with water and dried with sodium sulfate. Evaporation of the solution yields a half crystalline mass, which is boiled with ether (4 × 1000 ml). Unsolved product is disposed and the ether solutions are evaporated after filtration. An oil is obtained which soon crystallizes. Yield 86.0 g (58 %). Crystallization from chloroform yields the pure amine of m.p. 94.5° – 103°C. The hydrochloride is precipitated with hydrogene chloride from an ethanol solution. Crystallization from ethanol gives m.p. 239.5°C.

Example 31

2'-β-Dimethylaminoethyl-4-hydroxyspiro(cyclohexane-1,4'-isoquinoline)-1',3'-dione To the ketone from example 30 (3.14 g; 0.01 mole) in 100 ml of ethanol there is added sodium borohydride (0.19 g; 0.005 mole) under agitation. After 1.5 hours the mixture is acidified with 1 ml conc. hydrochloric acid. The ethanol is distilled off in vacuum and the obtained distillation residue is treated with saturated bicarbonate solution. The crystaline product is sucked off and crystallized from water. Yield 2.5 g (79 %). m.p. 140° – 143.5°C.

In one experiment a product of the same analysis as above but of m.p. 111.5° – 114°C was obtained. The two products are probably the trans- resp. cis-forms of the hydroxy compound.

EXAMPLE 32

2'-γ-Dimethylaminopropyl-4-hydroxyspiro(cyclohexane-1,4'-isoquinoline)-1',3'-dione To 4-hydroxyspiro(cyclohexane-1,4'-isoquinoline)-1',3'-dione (4.9 g; 0.02 mole) och γ-dimethylaminopropylchloride hydrochloride (3.16 g; 0.02 mole) in dimethylformamide (100 ml) there is added sodium hydride (50 % suspension in oil; 1.92 g; 0.04 mole) in portions under agitation. The mixture is stirred for 72 hours at 100°C, cooled to room temperature and poured on ice-water (500 ml). The product is extracted with ether. The combined ether extracts are shaken with 2 N hydrochloric acid. The hydrochloric acid solutions are cooled with ice and made alkaline with 40 % sodium hydroxide solution. The oil obtained is taken upp in ether, dried with potassium carbonate, filtered and released from the solvent. The free amine is obtained as an oil (5.2 g; 78 %) which crystallizes slowly. Crystallization from water yields a product of m.p. 119° – 121.5°C.

What we claim is:
1. A compound of the formula

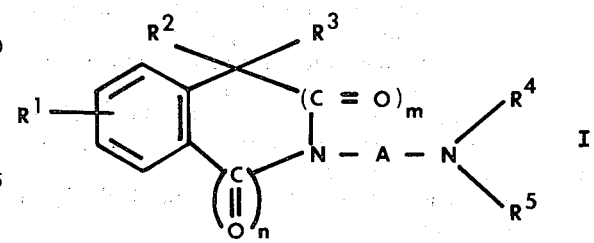

in which
m and n are each one, A is an ethylene or trimethylene group or such a group having a methyl substituent or A signifies an acetyl group or such a group having an α-alkyl substituent having 1-4 carbon atoms, connected to the group

by the carbonyl CO linkage,
$R^1$ is hydrogen, halogen or a nitro group,
$R^2$ and $R^3$ are saturated normal alkyl groups of up to 6 carbon atoms, or allyl or propargyl or taken together with the carbon atom to which they are bonded form a lower saturated carbocyclic ring, $R^4$ and $R^5$ are hydrogen or alkyl groups of at most 6 carbon atoms, or $R^4$ and $R^5$ together with the nitrogen form a pyrrolidine or a piperidine ring,
and, in case A is such an ethylene or trimethylene group, the corresponding amine oxides and quarternary lower alkyl ammonium compounds,
as well as salts of the basic compounds with non-toxic physiologically acceptable acids.

2. A compound of the formula

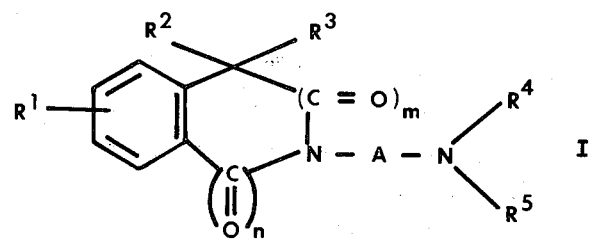

in which
m and n are each one, A is an ethylene or trimethylene group or such a group having a methyl substituent or A signifies an acetyl group or such a group having an α-alkyl substituent containing 1–4 carbon atoms, connected to the group

by the carbonyl CO linkage, $R^1$ is hydrogen, halogen or a nitro group, $R^2$ and $R^3$ are saturated normal alkyl groups of up to 6 carbon atoms, or allyl or propargyl or taken together with the carbon atom to which they are bonded form a lower saturated carbocyclic ring, $R^4$ and $R^5$ are hydrogen or alkyl groups of at most 6 carbon atoms, and, in case A is such an ethylene or trimethylene group, the corresponding amine oxides and quarternary alkyl ammonium compounds, as well as salts of the basic compounds with non-toxic physiologically acceptable acids.

3. A compound according to claim 1 wherein $R^2$ and $R^3$ are saturated normal alkyl groups of up to 6 carbon atoms or allyl or propargyl.

4. A compound according to claim 1, in which $R^2$ and $R^3$ signify methyl groups.

5. A compound according to claim 1, in which $R^2$ and $R^3$ together form a divalent tetramethylene or a divalent pentamethylene group.

6. A compound according to claim 1, in which A signifies a divalent ethylene or trimethylene group.

7. A compound according to claim 1, in which $R^4$ signifies a methyl group and $R^5$ signifies hydrogen or a methyl group.

8. The compound according to claim 1: 4,4-Dimethyl-2-β-methylaminoethylisoquinoline-1,3-dione.

9. The compound according to claim 1: 2-β-Dimethylaminoethyl-4,4l-dimethylisoquinoline-1,3-dione.

10. The compound according to claim 1: 4,4-Dimethyl-2-γ-methylaminopropylisoquinoline-1,3-dione.

11. The compound according to claim 1: 2-γ-Dimethylaminopropyl-4,4-dimethylisoquinoline-1,3-dione.

12. The compound according to claim 1: 2'-β-Methylaminoethylspiro (cyclopentane-1,4'-isoquinoline)-1',3'-dione.

13. The compound according to claim 1: 2'-β-Dimethylaminoethylspiro (cyclopentane-1,4'-isoquinoline)-1',3'-dione.

14. The compound according to claim 1: 2'-γ-Methylaminopropylspiro (cyclopentane-1,4'-isoquinoline)-1',3'-dione.

15. The compound according to claim 1: 2'-γ-Dimethylaminopropylspiro (cyclopentane-1,4'-isoquinoline)-1',3'-dione.

16. The compound according to claim 1: 2'-β-Methylaminoethylspiro (cyclohexane-1,4'-isoquinoline)-1',3'-dione.

17. The compound according to claim 1: 2'-β-Dimethylaminoethylspiro (cyclohexane-1,4'-isoquinoline)-1',3'-dione.

18. The compound according to claim 1: 2'-γ-Methylaminopropylspiro (cyclohexane-1,4'-isoquinoline)-1',3'-dione.

19. The compound according to claim 1: 2'-γ-Dimethylaminopropylspiro (cyclohexane-1,4'-isoquinoline)-1',3'-dione.

20. Quarternary addition products of the compounds according to claim 1 with dimethyl sulphate and lower alkyl halides with 1 to 3 carbon atoms.

21. A compound according to claim 1: 2-(4,4-dimethylisoquinoline-1,3-dione)-acetamide and salts thereof with physiologically acceptable acids.

22. A compound according to claim 1: 2'-spiro (cyclopentane-1,4'-isoquinoline)-1',3'-dione-acetamide and salts with physiologically acceptable acids.

* * * * *